United States Patent [19]
Mathson

[11] Patent Number: 6,021,350
[45] Date of Patent: Feb. 1, 2000

[54] IMPLANTABLE HEART STIMULATOR WITH A MAXIMUM STIMULATION RATE THAT IS ADJUSTED DEPENDENT ON ISCHEMIA DETECTION

[75] Inventor: Göran Mathson, Uppsala, Sweden

[73] Assignee: Pacesetter AB, Solna, Sweden

[21] Appl. No.: 09/048,490

[22] Filed: Mar. 26, 1998

[30] Foreign Application Priority Data

Mar. 26, 1997 [SE] Sweden ................... 9701121

[51] Int. Cl.$^7$ ................... A61N 1/365
[52] U.S. Cl. ................... 607/17; 607/9
[58] Field of Search ................... 607/9, 17, 24

[56] References Cited

U.S. PATENT DOCUMENTS 5,076,271 12/1991 Lekholm et al. .
5,195,518 3/1993 Mannion et al. ................... 607/17
5,199,428 4/1993 Obel et al. .
5,531,768 7/1996 Alferness .

FOREIGN PATENT DOCUMENTS

| 0 108 731 | 5/1984 | European Pat. Off. . |
| 0 140 472 | 5/1985 | European Pat. Off. . |
| 0 545 628 | 6/1993 | European Pat. Off. . |
| WO 92/16257 | 10/1992 | WIPO . |

*Primary Examiner*—William E. Kamm
*Assistant Examiner*—George R. Evanisko
*Attorney, Agent, or Firm*—Hill & Simpson

[57] ABSTRACT

An implantable heart stimulator includes a unit for setting a maximum allowable stimulation rate and an ischemia detector. An analysis unit and control unit and connected to the ischemia detector and to the setting unit for controlling the setting unit so as to lower the maximum allowable stimulation rate in response to the detection of an ischemic state.

17 Claims, 2 Drawing Sheets

IMPLANTABLE HEART STIMULATOR WITH A MAXIMUM STIMULATION RATE THAT IS ADJUSTED DEPENDENT ON ISCHEMIA DETECTION

BACKGROUND OF THE INVENTION

1. Field of the Invention

The present invention relates to an implantable heart stimulator of the type having means for setting a maximum allowable stimulation rate, and an ischemia detector.

2. Description of the Prior Art and Related Subject Matter

Ischemia is a condition resulting from insufficient blood flow through the heart muscle. The reason therefor is blocking or passage congestion of coronary blood vessels of the heart. Blood penetration of the heart muscle is possible only in the diastolic phase, that is the phase between two consecutive contractions of the heart, when the aortic valve is closed. About 60% of the oxygen content inside the heart tissue is consumed during a heart contraction and in order to maintain the pumping efficiency of the heart the consumed oxygen must be refilled until the next contraction.

An increased heart rate results in only minor shortening of the systolic phase, that is the contraction phase of the heart, and consequently an increased heart rate results mainly in a shortening of the diastolic phase, which is the period during which oxygen is supplied to the heart as mentioned above. An increased workload will consequently worsen the situation for an ischemic patient.

In such a situation a symptomatic (episodic) ischemia, that is angina pectoris, heart insufficiency or infarct, will force the patient, because of the associated pain, to stillness, with a reduced heart rate as a consequence.

No heart stimulators, like pacemakers, are able to react to pain, and so called rate response pacemaker systems responding to metabolical, hemodynamical or activity inputs will try to compensate for the oxygen deficiency of the heart by increasing the stimulation rate, thus worsening the ischemic situation of the patient.

In U.S. Pat. No. 5,199,428 a technique is described for detecting ischemia and both effecting stimulation of nerves regulating blood pressure and heart rate to reduce the heart's oxygen requirements while providing pacing therapies to maintain the patient's heart rate within acceptable limits, e.g. to overcome bradyarrhythmia and/or unphysiological AV-delays induced by the nerve stimulation.

A large portion of cardiac ischemia is silent. It has been suggested that up to 80% of ischemic heart diseases are silent, i.e. a state of ischemia which the patient is not aware of. Rate modulated pacing is used to override the poor sinoatrial response of the patient to exercise which, in this case, is physiological.

It has also been proposed to provide heart stimulators provided with an ischemia detector to lower the actual stimulation rate in response to the detection of an ischemic episode, in order to slow down or stop the further development of the ischemia (see Swedish Patent Application SE 9700182-0, filed Jan. 23, 1997, or corresponding PCT application PCT/SE98/0043, filed Jan. 13, 1998, both of these applications being unpublished as of the filing date for the present application.

In rate modulated pacing systems a programmable value sets the highest pacing rate that can be achieved in response to sensor input, the so-called maximum sensor rate (MSR). In an ischemic situation a sensor which is sensing e.g. the physical activity level of the patient, e.g. an accelerometer, can often increase the stimulation rate, as discussed above. When a sensor is controlling the pacing rate in this way, the pacing rate thus will not exceed the programmed maximum sensor rate for the sensed level of activity.

In a dual-chamber sensing and tracking pacing system in which the ventricle is stimulated with a certain delay in response to a detected atrial activity normally a programmable value sets the highest allowable ventricular pacing rate, the so-called maximum tracking rate (MTR) Conventionally the maximum sensor rate and the maximum tracking rate are set so high that in an ischemic situation the pacing system can stimulate the heart to an infarct.

SUMMARY OF THE INVENTION

An object of the present invention is to provide an implantable heart stimulator in which the aforementioned disadvantages of known stimulators are avoided.

The above object is achieved in accordance with the principles of the present invention in an implantable heart stimulator having a unit for setting a maximum allowable stimulation rate and an ischemia detector, with an analysis unit and a control unit connected to the ischemia detector and the setting unit, for controlling the setting unit so as to lower the maximum allowable stimulation rate in response to the detection of an ischemia.

Thus in response to the detection of an ischemia the maximum allowable stimulation rate, like the maximum sensor rate or the maximum tracking rate, is decreased. Because stimulation at higher rates is most disastrous to an ischemic patient the lowering of the maximum allowable stimulation rate is an effective measure for avoiding an aggravation of ischemia and can even improve an ischemic situation. Myocardial infarction due to inappropriately high upper rates in rate modulated pacing is consequently avoided.

The values of MSR and MTR, that are initially programmed when a stimulator is implanted, are very much dependent on the age and the condition of the patient; typical values are in the ranges of 130–140/minute up to 160–170/minute. When an ischemic episode is detected the MSR/MTR are lowered to approximately 100–120/minute.

According to an embodiment of the stimulator of the invention the ischemia detector is an ischemia analyzer for detecting an ischemia by analysis of recorded IECGs or ECGs. Body surface ECG diagnostics for determining ischemic states are well known and are facilitated if ventricular pacing is performed in the upper parts of the septum. In this case the depolarization is spread through the normal conduction system, e.g. the bundle branches and Purkinje fibers. The evoked response will then on a surface ECG look like a normally conducted QRS and detection of an ischemia, e.g. from elevation of the ST-segment above a base line, is facilitated. The ECG used can be a synthesized "surface" ECG, i.e. an electrocardiogram synthesized from signals picked up by the implanted electrodes. This is a known technique, which makes an advantageous embodiment of the stimulator according to the invention possible, since no external recording equipment is needed but only already implanted means. For the same reason it is also suitable to determine an ischemia by analyzing IECGs. The technique for IECG sensing is well established as well.

In another embodiment of the heart stimulator of the invention, the ischemia analyzer is disposed to detect an ischemic episode by analysis of heart rate variability from recorded IECGs or ECGs. Normally heart beat intervals, AV-conduction intervals and QRS-amplitudes are subject to variations. Heart rate variation is at a maximum for a healthy individual at rest. Activity of the individual or reduced capacity due to insufficiency or illness is reflected as a decrease in the heart rate variability and this defect can be used for ischemia detection.

It is known that the heart wall becomes thicker and stiffer as a result of an ischemic episode. The accompanying change in the moving pattern of the heart wall can be detected by measuring different parameters and used for detection of an ischemic situation. Thus, according to another embodiment of the heart stimulator of the invention, the ischemia detector is a lead bend sensor located at the distal end portion of the lead, used for detection of an ischemia from the ability of the ventricle to contract and expand. Thus, with such a sensor the reduced ability of the ventricles to contract and expand can be detected as an indication of an ischemic episode. Alternatively, the ischemia detector can be an arrangement for measuring the AC-impedance in the ventricle. The magnitude of the AC-impedance is a measure of the blood filling of the ventricle and consequently such an impedance measurement can be used for detecting an ischemic situation. According to another embodiment of the heart stimulator of the invention, the ischemia detector can be an arrangement for measuring sound absorption in the heart tissue. Sound absorption is effected by changes in the stiffness of the heart tissue and the sound absorption measuring arrangement can be provided to determine e.g. the absorption of sound waves generated by the valve closure as they propagate from the upper portion of the ventricle to the apex region.

Because an ischemia degrades the efficiency of the pumping of the heart, an ischemic situation can be detected by studying blood pressures and cardiac outputs. Thus, according to a further embodiment of the invention, the ischemia detector is an arrangement for measuring the difference between systolic and diastolic pressures and comparing this difference, obtained from one heartbeat, to the difference obtained from the next heartbeat.

An ischemic state is normally associated with severe pain forcing the patient to sit down or lie down with a reduced heart rate as a consequence. At the same time the patient feels a need for forced breathing, known as hyperventilation. This unusual combination of the needs of an ischemic patient can be used for detecting the ischemic episode. Thus, according to another embodiment of the stimulator of the invention the ischemia detector is patient workload sensor and a patient breathing sensor, which for detect an ischemia from the occurrence of a predetermined relation between sensed workload and sensed breathing activity.

DESCRIPTION OF THE PREFERRED EMBODIMENTS

Figure 1:
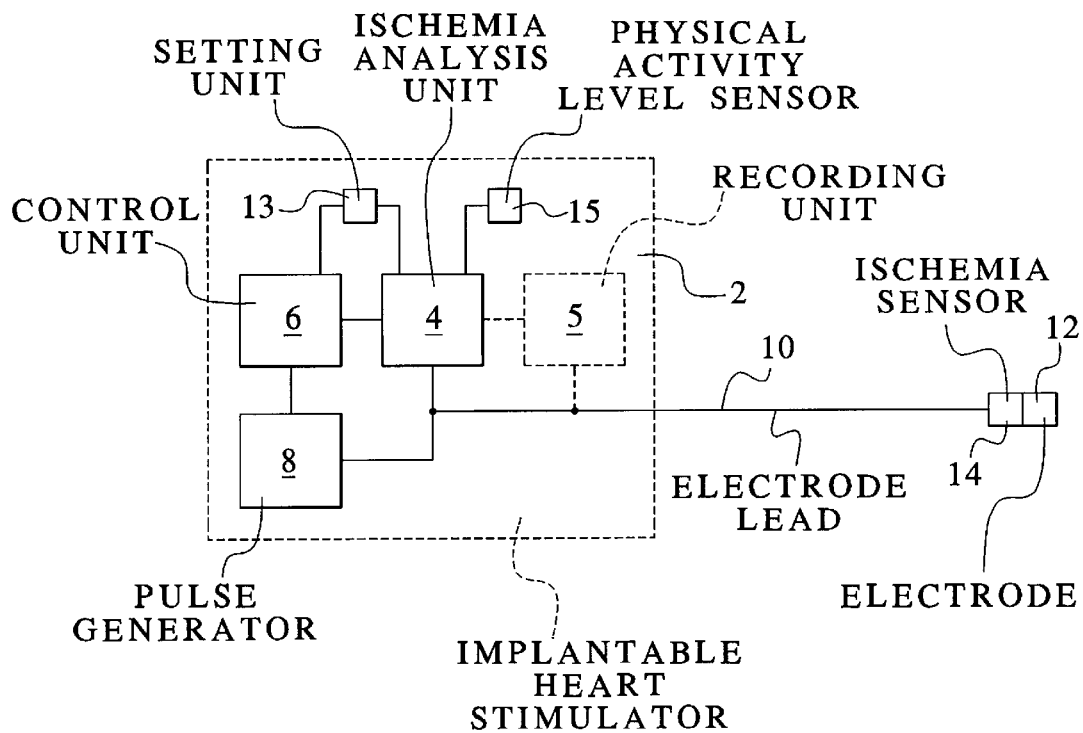
FIG. 1 is a simplified block diagram of a heart stimulator according to the invention.

FIG. 1 is a simplified block diagram of an implantable heart stimulator 2 according to the invention. The heart stimulator 2 includes an ischemia analysis unit 4 and a control unit 6, connected to the ischemia analysis unit 4. The control unit 6 is connected to a pulse generator 8 for controlling the rate of generated stimulation pulses. The pulse generator 8 is connected to a lead 10 provided with electrodes 12 at the distal end portion for delivery of stimulation pulses and possible electrical measurements, the lead 10 being intended for implantation into the heart of a patient. A sensor 14 for ischemia detection is also provided at the distal end portion of the lead 10 and sensing signals are supplied to the ischemia analyzing unit 4 through the lead 10 as well.

As will be described more in detail below an ischemic state can be detected by IECGs and ECGs. For recording IECGs the sensor 14 has electrodes and electrical signals are supplied by the lead 10 to a recording unit 5 which is connected to the ischemia analysis unit 4 for further analysis of the IECGs.

As an alternative the recording unit 5 can be a unit for synthesizing "surface" ECGs from signals received from the implanted sensor 14. In this way ECGs are obtained which are similar to externally recorded surface ECGs.

A setting unit 13 is also provided for setting a maximum allowable stimulation rate. The setting unit 13 is connected to the ischemia analysis unit 4 and to the stimulation rate control unit 6 and causes the stored maximum allowable stimulation rate to be lowered in response to the detection of an ischemia.

The maximum allowable stimulation rate remains in its lowered state for at least as long as the state of ischemia is present, and possibly for a predetermined period of time after the state of ischemia has terminated, e.g. 5–10 min.

The heart stimulator 2 can include a physical activity level sensor 15 which emits an electrical signal indicative of a level of physical activity. The physical activity level sensor 15 can be e.g. an accelerometer for sensing body movements of the patient or a sensor for sensing muscular sounds of the patient, and is connected to the ischemia analysis unit 4. Alternatively the sensor 15 can be a metabolic demand sensor for sensing metabolic changes, like changes in nutrition and oxygen consumption of the patient for controlling the stimulation rate accordingly. In this case the maximum allowable stimulation rate is equal to the maximum rate associated with the sensed level of activity. In the case of dual-chamber pacing, the maximum sensor rate is determining both for atrial and ventricular stimulation.

As another alternative, in dual-chamber sensing and tracking modes the sensor 14 can be positioned in the atrium for sensing atrial activity for controlling the stimulation of the ventricle by the electrode 12. In this case the setting unit 13 can be arranged to set the maximum allowable stimulation rate equal to the maximum tracking rate.

Of course the heart stimulator 2 can include both an activity or metabolic sensor 15 and a sensor 14 for tracking modes. Since the maximum sensor rate may be programmed lower than, equal to or greater than the maximum tracking rate, the setting unit 13 is in this case disposed to select the lower one of these two rates as the maximum allowable stimulation rate.

Figure 2:
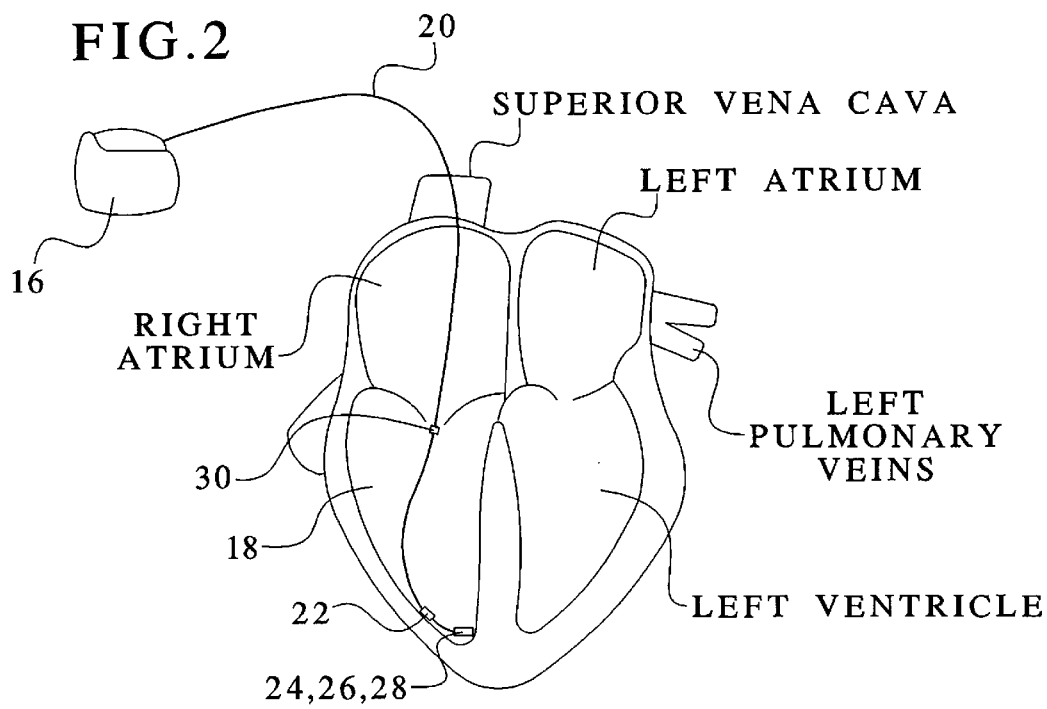
FIG. 2 illustrates a pacemaker with its lead implanted in a conventional way in the right ventricle, said lead having stimulation electrodes and sensing means for the ischemia detector.

FIG. 2 shows an implanted heart stimulator in the form of a pacemaker 16, connected to the right ventricle of the heart of a patient by its lead 20. The electrode is of a bipolar type with an electrode ring 22 and a tip electrode 24 and a pressure sensor 26 is provided at a distal end portion of the lead 20 as well.

Figure 3:
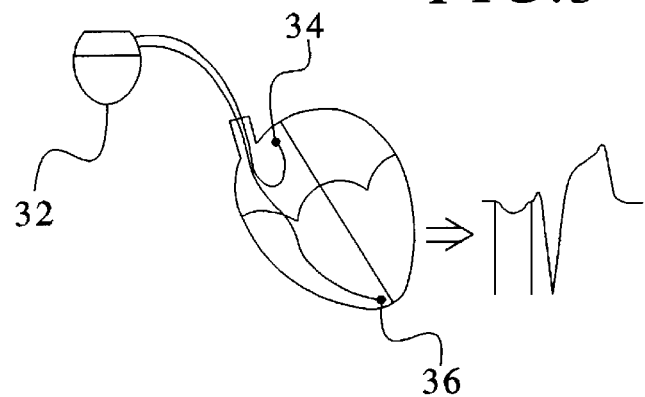
FIGS. 3 and 4 show schematically a pacemaker with leads implanted in the atrium and the ventricle in a conventional way and with the ventricular lead electrode positioned in the upper parts of the septum, respectively.

FIG. 3 shows a pacemaker 32 for dual-chamber pacing and/or sensing with electrode poles 34, 36 positioned in a conventional manner in the atrium and the ventricle, respectively. In case of stimulation both in the atrium and the ventricle the corresponding evoked response appearing on a (synthesized) surface ECG is shown in the same figure.

Figure 4:
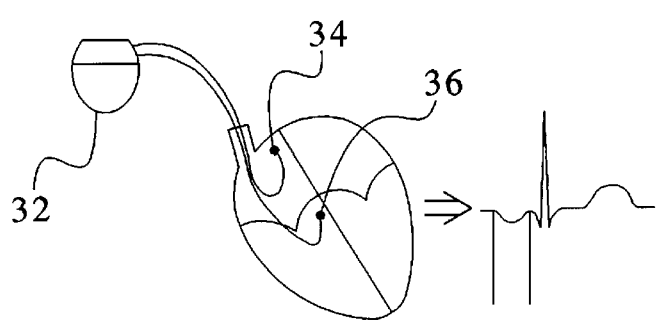

In FIG. 4 the ventricular electrode pole 36 is positioned in the upper part of the septum. This is an advantageous position of the electrode pole 36, since it will then be possible for the depolarization to propagate through the normal conduction system, e.g. the bundle branches and Purkinje fibers. The evoked response will then on surface ECGs look like normally conducted QRS, as appears from the ECG shown in FIG. 4.

For the detection of an ischemia different techniques can be used. For an implantable heart stimulator an analysis of recorded IECG is a suitable method for ischemia detection, as mentioned above. The electrodes 22, 24 of the already implanted electrode lead 20, of FIG. 2, can then be used for recording the IECG. The signals received by the electrodes 22, 24 can also be used for synthesizing "surface" ECGs to be used for detection of an ischemic state.

Figure 5:
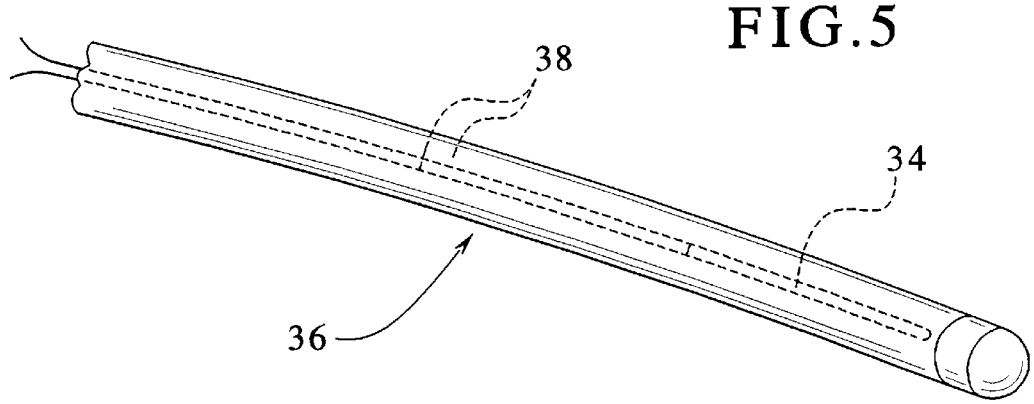
FIG. 5 shows a lead bend sensor for the ischemia detector.

It is known that the heart wall becomes thicker and stiffer as a result of an ischemic state. Thus an ischemic situation can be detected by studying changes in the moving pattern of the heart wall. In FIG. 5 a lead bend sensor 34 is shown located at the distal end portion of a lead 36. This bend sensor 34 can be formed of e.g. a piezoelectric material which generates an electric signal when subjected to bending movements, the signal being supplied to the ischemia analysis unit 4, see FIG. 1, through conductors 38.

An ischemia can also be detected by AC-impedance measurements in the ventricle 18, since this impedance is related to the blood filling of the ventricle. For this impedance measurement the electrodes 22, 24 of the lead 20, see FIG. 2, can be used and the measurement signals are supplied to the ischemia analysis unit 4 through the conductors of the lead 20. Further, an ischemia can be detected from the sound absorption in the heart tissue, since this absorption changes with changes in the stiffness of the heart tissue. Thus, one microphone 28 is mounted at the distal end of the lead 20 and another microphone 30 is mounted on the lead 20 such that it will be positioned in the upper part of the ventricle 18 after implantation of the lead, see FIG. 2. In this way it is possible to measure the absorption of sound waves generated at the upper part of the ventricle 18 by valve closure during propagation through the ventricle 18 down to the microphone 28 situated at the ventricular bottom. The signals picked up by the microphones 28, 30 are fed to the ischemia analysis unit 4 for analysis.

An ischemia can be detected by studying blood pressures and cardiac outputs as well, since an ischemia will affect the efficiency of the pumping of the heart. Thus an ischemic episode can be determined by measuring the difference between the systolic and the diastolic pressures and comparing this difference from one heartbeat to the difference obtained from the next heartbeat. An ischemic episode can also be detected by monitoring the systolic pressure over time. For these pressure measurements the pressure sensor 26 in FIG. 2 is used. The pressure signals obtained from the pressure sensor 26 is supplied through the lead 20 to the ischemia analysis unit 4.

An ischemic episode can also be detected by studying the cardiac output. For this purpose a flow sensor can be positioned e.g. in the pulmonary artery for measuring the cardiac output.

An ischemic episode can further be detected by studying the patient workload and the patient breathing activity. The workload can be sensed by e.g. the activity sensor 15 and the breathing activity can be determined by measuring e.g. the AC-impedance between the two electrodes 22, 24 of the electrode lead 20, or between one of the electrodes 22, 24 and the case of the pacemaker 16, cf. FIG. 2. An ischemic episode is then detected from the occurrence of a predetermined relation between sensed workload and sensed breathing activity.

Another way of detecting an ischemic episode is to monitor sensed repolarization of the heart and patient workload. Information about repolarization of the heart is obtained from IECGs and ECGs and patient workload sensing means can be undertaken using e.g. an activity sensor. An ischemic state is then detected from the occurrence of a predetermined relation between sensed repolarization and sensed workload.

Other techniques for detecting an ischemic state are known to those skilled in the art. One or more of the above described methods for ischemia detection can be combined to obtain an improved reliability in the ischemia detection.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable heart stimulator comprising:
   a pulse generator which emits stimulation pulses at a stimulation rate;
   setting means, connected to said pulse generator, for setting a maximum allowable stimulation rate;
   an ischemia detector which detects a state of ischemia; and
   means connected to said ischemia detector and to said setting means for controlling said setting means for lowering said maximum allowable stimulation rate upon a detection of a state of ischemia by said ischemia detector.

2. An implantable heart stimulator as claimed in claim 1 further comprising:
   an activity sensor which senses a level of physical activity of a subject and which emits an electrical signal identifying said level of physical activity; and
   said means for controlling comprising means for controlling said setting means for setting said maximum allowable stimulation rate, in an absence of a detection of a state of ischemia, to a maximum stimulation rate programmed for the sensed level of activity.

3. An implantable heart stimulator as claimed in claim 1 further comprising:
   a metabolic demand sensor which senses metabolic senses metabolic demand of a subject and which emits an electrical signal indicative of an activity level of a subject dependent on the senses metabolic demand; and
   said means for controlling comprising means for controlling said setting means for setting said maximum allowable stimulation rate, in an absence of a detection of a state of ischemia, to a maximum stimulation rate programmed for the sensed level of activity.

4. An implantable heart stimulator as claimed in claim 1 further comprising:
   means for sensing atrial electrical activity in an atrium;
   means for delivering said stimulation pulses to a ventricle at a ventricular stimulation rate;
   said means for controlling comprising means for controlling said ventricular stimulation rate dependent on said atrial electrical activity and said ventricular stimulation rate having a maximum tracking rate associated therewith; and said control means comprising means for setting said maximum allowable stimulation rate equal to said maximum tracking rate.

5. An implantable heart stimulator as claimed in claim 1 wherein said ischemia detector comprises means for recording recorded signals selected from the group consisting of IECGs and ECGs, and means for detecting a state of ischemia by analyzing said recorded signals.

6. An implantable heart stimulator as claimed in claim 5 wherein said recorded signals have a baseline and contain ST segments and T waveforms, and wherein said means for detecting comprises means for identifying a state of ischemia dependent on an elevation from said baseline of said ST segments and said T waveforms in said recorded signals.

7. An implantable heart stimulator as claimed in claim 5 wherein said recorded signals contain T waveforms, and wherein said means for detecting comprises means for identifying a state of ischemia dependent on said T waveforms in said recorded signals.

8. An implantable heart stimulator as claimed in claim 5 wherein said means for detecting comprises means for identifying a state of ischemia dependent on heart rate variability identified from said recorded signals.

9. An implantable heart stimulator as claimed in claim 1 further comprising:

an electrode lead connected to said pulse generator for delivering said stimulation pulses to a heart, said lead experiencing bendings due to cardiac activity of said heart; and said ischemia detector comprising a lead bending sensor disposed at a distal end of said lead and means for identifying a state of ischemia dependent on a frequency and amplitude of bending of said lead.

10. An implantable heart stimulator as claimed in claim 1 wherein said ischemia detector comprises means for measuring an AC impedance in a ventricle.

11. An implantable heart stimulator as claimed in claim 1 wherein said ischemia detector comprises means for measuring sound absorption in heart tissue.

12. An implantable heart stimulator as claimed in claim 1 wherein said ischemia detector comprises means for measuring a difference between systolic and diastolic pressures respectively in successive heartbeats, and for comparing a difference obtained from one heartbeat to a difference obtained from a next successive heartbeat.

13. An implantable heart stimulator as claimed in claim 1 wherein said ischemia detector comprises a flow sensor which identifies cardiac output.

14. An implantable heart stimulator as claimed in claim 1 wherein said ischemia detector comprises means for sensing a patient workload and means for sensing patient respiration, and means for detecting a state of ischemia dependent on an occurrence of a predetermined relation between said workload and said respiration.

15. An implantable heart stimulator as claimed in claim 1 wherein said ischemia detector comprises means for sensing repolarization of a heart and means for sensing patient workload, and means for identifying a state of ischemia from an occurrence of a predetermined relation between said repolarization and said workload.

16. An implantable heart stimulator as claimed in claim 1 wherein said means for controlling comprises means for lowering said maximum allowable stimulation rate to a stimulation rate in a range between 100 and 110 stimulation pulses per minute.

17. An implantable heart stimulator as claimed in claim 16 wherein said means for controlling comprises means for maintaining said maximum allowable stimulation rate at a lowered rate for at least as long as said state of ischemia is present.

* * * * *